United States Patent
Zörnack et al.

(10) Patent No.: US 9,758,195 B2
(45) Date of Patent: Sep. 12, 2017

(54) SPRING STRUT TOP MOUNTING

(71) Applicant: THYSSENKRUPP STEEL EUROPE AG, Duisburg (DE)

(72) Inventors: Markus Zörnack, Dortmund (DE); Stephan Drewes, Mönchengladbach (DE)

(73) Assignee: THYSEENKRUPP STEEL EUROPE AG, Duisburg (DE)

( * ) Notice: Subject to any disclaimer, the term of this patent is extended or adjusted under 35 U.S.C. 154(b) by 0 days.

(21) Appl. No.: 14/677,439

(22) Filed: Apr. 2, 2015

(65) Prior Publication Data
US 2015/0284029 A1 Oct. 8, 2015

(30) Foreign Application Priority Data
Apr. 4, 2014 (DE) .................. 10 2014 104 838

(51) Int. Cl.
*B62D 25/08* (2006.01)
*B62D 27/02* (2006.01)
(Continued)

(52) U.S. Cl.
CPC .............. *B62D 25/088* (2013.01); *A61L 2/26* (2013.01); *B62D 27/02* (2013.01); *F16L 33/28* (2013.01);
(Continued)

(58) Field of Classification Search
CPC .... B62D 25/088; B62D 27/02; B62D 25/082; A61L 2/26; A61L 2202/123; F16L 33/28; F16L 37/26; F16L 2201/40
See application file for complete search history.

(56) References Cited

U.S. PATENT DOCUMENTS 3,596,978 A * 8/1971 Wessells, III ........ B62D 25/087
296/203.02
4,465,296 A * 8/1984 Shiratori .............. B60G 15/068
267/220
(Continued)

FOREIGN PATENT DOCUMENTS

CN 102470900 A 5/2012
CN 102791564 A 11/2012
(Continued)

OTHER PUBLICATIONS

English language Abstract for JP 2013189102 A.
(Continued)

*Primary Examiner* — Karen Beck
(74) *Attorney, Agent, or Firm* — thyssenkrupp North America, Inc.

(57) ABSTRACT

The invention relates to a spring strut top mounting, comprising at least one shaping base body, wherein the at least one shaping base body has a dome-shaped section in the region connecting to the spring strut and at least one separate, local reinforcement element which is connected to the base body. The object of making available a spring strut top mounting which has improved rigidity, in particular improved local rigidity, is achieved according to the invention in that the base body has at least one stamped region in the region connecting to the spring strut, and the at least one reinforcement element lays against the base body at least in the vicinity of the at least one stamped region.

19 Claims, 3 Drawing Sheets

(51) Int. Cl.
  *F16L 33/28* (2006.01)
  *F16L 37/26* (2006.01)
  *A61L 2/26* (2006.01)

(52) U.S. Cl.
  CPC ......... *F16L 37/26* (2013.01); *A61L 2202/123* (2013.01); *F16L 2201/40* (2013.01)

(56) References Cited

U.S. PATENT DOCUMENTS

| | | | | |
|---|---|---|---|---|
| 4,981,287 A * | 1/1991 | Cothenet | ............... | B60G 13/001 |
| | | | | 267/153 |
| 5,456,517 A * | 10/1995 | Kalian | ................ | B60G 15/068 |
| | | | | 164/47 |
| 5,580,121 A * | 12/1996 | Dange | ................ | B62D 25/088 |
| | | | | 296/181.4 |
| 6,260,836 B1 * | 7/2001 | Aoyama | .............. | B60G 15/063 |
| | | | | 267/179 |
| 6,908,076 B2 * | 6/2005 | Hayashi | ............... | B60G 13/003 |
| | | | | 267/153 |
| 7,390,047 B2 * | 6/2008 | Hanakawa | ........... | B62D 25/081 |
| | | | | 296/203.02 |
| 8,746,784 B2 * | 6/2014 | Hanakawa | ........... | B62D 25/088 |
| | | | | 296/187.09 |
| 8,814,188 B2 * | 8/2014 | Anh | ........................ | B62D 21/09 |
| | | | | 267/220 |
| 8,870,274 B2 * | 10/2014 | Mildner | ................. | B62D 25/02 |
| | | | | 296/187.11 |
| 9,033,400 B2 * | 5/2015 | Sasaki | .................... | B62D 25/08 |
| | | | | 296/187.09 |
| 9,156,501 B2 * | 10/2015 | Mildner | ................. | B62D 21/11 |
| 2012/0242111 A1 | 9/2012 | Mildner et al. | | |
| 2014/0097590 A1 * | 4/2014 | Yoo | ...................... | B62D 25/088 |
| | | | | 280/124.155 |
| 2014/0292028 A1 * | 10/2014 | Dix | ...................... | B62D 25/088 |
| | | | | 296/187.1 |
| 2015/0251703 A1 * | 9/2015 | Yamada | ............... | B62D 25/087 |
| | | | | 296/187.12 |
| 2016/0264176 A1 * | 9/2016 | Balzer | ................... | B62D 21/11 |

FOREIGN PATENT DOCUMENTS

| | | | | |
|---|---|---|---|---|
| DE | 10033712 A1 * | 1/2002 | ............. | B60G 11/16 |
| DE | 10108171 A1 * | 8/2002 | .......... | B62D 25/088 |
| DE | EP 2353974 A2 * | 8/2011 | .......... | B62D 25/088 |
| DE | WO 2014183976 A1 * | 11/2014 | .......... | B62D 25/088 |
| DE | 102013105867 A1 * | 12/2014 | ............. | B21K 23/00 |
| DE | 102013014704 A1 * | 3/2015 | .......... | B62D 25/088 |
| EP | 0940320 A1 | 9/1999 | | |
| FR | 2221295 A1 * | 10/1974 | ............. | B60G 3/265 |
| FR | DE 19941907 A1 * | 3/2000 | ............. | B62D 21/11 |
| JP | H0930370 A | 2/1997 | | |
| JP | H0995262 A | 4/1997 | | |
| JP | 2713421 B2 * | 2/1998 | .......... | B65D 25/088 |
| JP | 2004306883 A | 11/2004 | | |
| JP | EP 2433850 A1 * | 3/2012 | .......... | B62D 25/088 |
| JP | 2013189102 A | 9/2013 | | |

OTHER PUBLICATIONS

English language Abstract for JP H0995262 A.
English language Abstract for CN 102791564 A.
English language Abstract for JP H0930370 A.
English language Abstract for JP 2004306883 A.
English language Abstract for EP 0940320 A1.

* cited by examiner

SPRING STRUT TOP MOUNTING

CROSS-REFERENCE TO RELATED APPLICATIONS

This application claims priority to German Patent Application Serial No. DE 102014104848.5 filed Apr. 4, 2014, the entire contents of which are hereby incorporated by reference herein.

FIELD

This disclosure relates to a spring strut top mounting, comprising at least one shaping base body, wherein the at least one shaping base body has a dome-shaped section in the region connecting to the spring strut, and at least one separate, local reinforcement element which is connected to the base body.

BACKGROUND

Spring strut top mountings which have a reinforced base body in order to increase their local rigidity are known from the prior art, for example from German laid-open patent application DE 101 08 171 A1. This document discloses a spring strut top mounting composed of a base body and a reinforcement which is embodied as a separate component and is connected in the region of high loading, specifically in the region connecting to the spring strut, to the base body. In this context, the shell-shaped reinforcement is bonded to the base body by means of an adhesive gap.

Since it is desirable to have the largest possible degree of rigidity for the spring strut top mountings, there is a need for improvement in the rigidity of spring strut top mountings currently in use in the industry and known in the prior art.

SUMMARY

It is an object of the present disclosure to make a spring strut top mounting having improved rigidity, in particular improved local rigidity. In one aspect of the present disclosure, an embodiment of a spring strut top mounting includes at least one base body having a dome-shaped section defined in a region that is configured to be coupled to the spring strut, and at least one stamped region formed in the region configured to be coupled to the spring strut. The spring strut top mounting further includes at least one separate local reinforcement element coupled to the at least one base body, and laying against the at least one base body at least in a vicinity of the at least one stamped region.

BRIEF DESCRIPTION OF THE DRAWINGS

The present invention is described in detail below with reference to the attached drawing figures, wherein.

DETAILED DESCRIPTION

Figure 1:
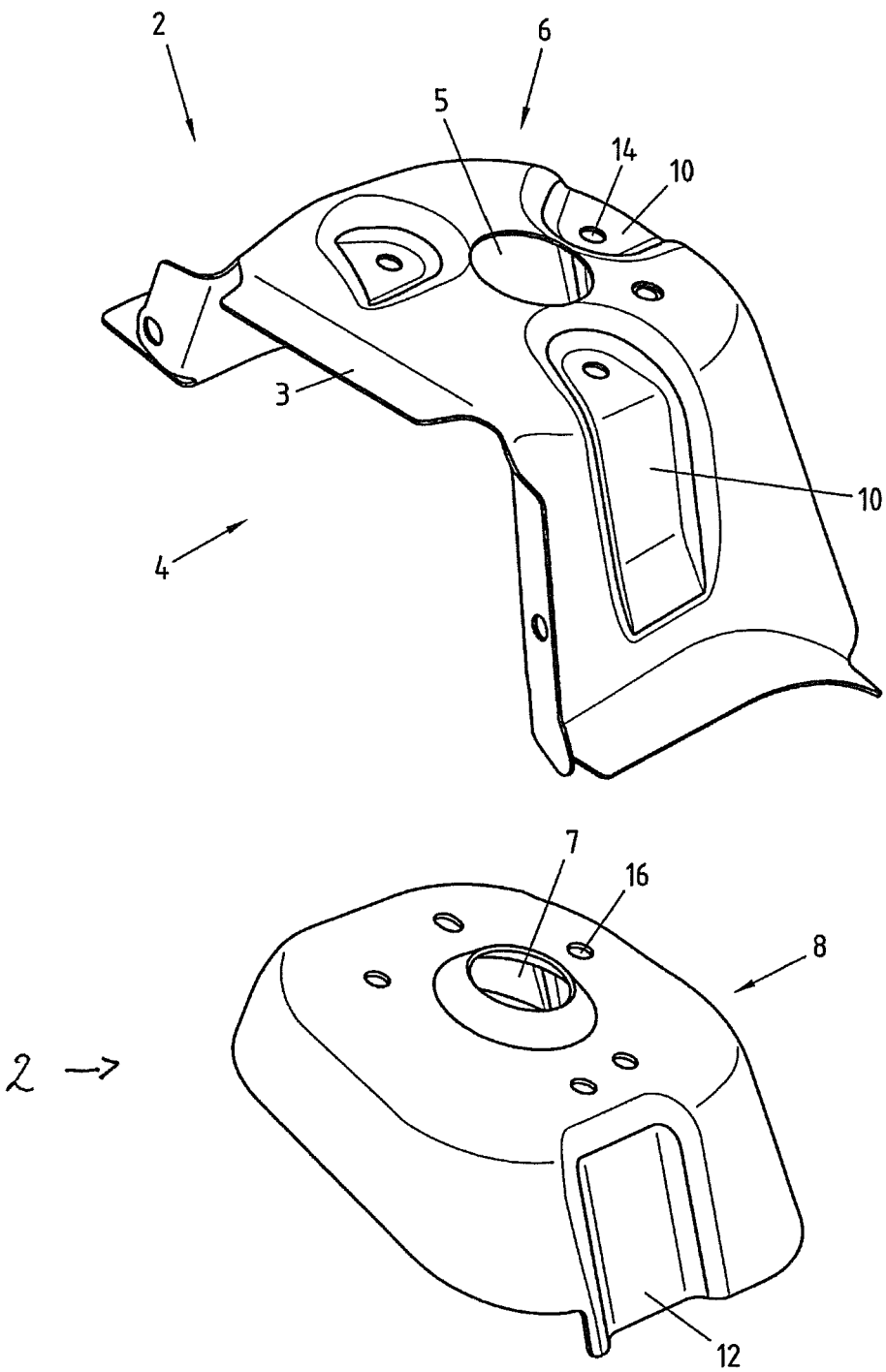
FIG. 1 is an isometric exploded view of an embodiment of a spring strut top mounting of the present disclosure having a base body and a reinforcing element.

Various embodiments now will be described more fully hereinafter with reference to the accompanying drawings, which form a part hereof, and which show, by way of illustration, specific embodiments. However, the present disclosure may be embodied in many different forms and should not be construed as limited to the embodiments set forth herein. Rather, these embodiments are provided so that this disclosure will be thorough and complete, and will fully convey the scope of the invention to those skilled in the art. The following detailed description is not to be taken in a limiting sense.

Throughout the specification and claims, the following terms take the meanings explicitly associated herein, unless the context clearly dictates otherwise. The phrase "in one embodiment" does not necessarily refer to the same embodiment, although it may. Furthermore, the phrase "in another embodiment" does not necessarily refer to a different embodiment, although it may. Thus, as described below, various embodiments may be readily combined without departing from the scope or spirit of the present disclosure.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Presently disclosed herein is a spring strut top mounting. The spring strut top mounting includes a base body having at least one stamped region in the region connecting to the spring strut, and at least one reinforcement element coupled to and laying against the base body at least in the vicinity of the at least one stamped region.

A shaping base body is understood according to the present disclosure to be a base body which has at least one dome-shaped section in the region connecting to the spring strut. In addition, the base body also has a region connecting to the bodywork of the vehicle. The at least one stamped region is disposed at least partially in the dome-shaped section of the base body.

In this context, the at least one stamped region can also extend beyond the dome-shaped section, with the result that a particularly large area can be made available for the connection to the reinforcement element. As a result of the geometric configuration of the base body, specifically as a result of the presence of the at least one step-shaped stamped region, the rigidity of the base body can be increased substantially.

This is because generally the rigidity of a component is determined, on the one hand, by the material properties and, on the other hand, by its geometric configuration. Consequently, a component with a complex geometry can have a greater rigidity than components of simple design.

This increased rigidity based on the geometry of the base body is combined with a further improvement of the rigidity by means of at least one local doubling of material in the region connecting to the spring strut or in the region connecting to the bodywork of the vehicle. This is because of the fact that, as a result of the reinforcement element laying against the base body at least in the vicinity of the stamped regions, it is possible to achieve a further increase in the rigidity in the relevant region of the spring strut top mounting which is particularly subject to high loading. At the same time, the material thickness of the base body can be reduced, with the result that the inventive configuration of the spring strut top mounting additionally permits a saving in terms of material and therefore weight to be achieved.

As a result of improved rigidity, in particular as a result of particularly high local rigidity in the loaded regions, it is possible, according to the invention, to avoid or reduce the introduction of stresses into the spring strut top mounting, for example resulting from a change in shape of the spring strut top mounting. In addition, the inputting of energy into the vehicle bodywork, in particular if vibrations or shocks are transmitted to the spring strut top mounting by the spring strut, can be reduced by the particularly high local rigidity at the corresponding coupling points. As a result, it is possible, by improving the rigidity of the spring strut top mounting, on the one hand to improve the service life of this component and, on the other hand, to make available improved driving comfort for the vehicle occupants, in particular with respect to the vibration behavior of the vehicle.

Both the base body and the reinforcement element coupled thereto have, in the region connecting to the spring strut, a cutout for receiving the spring strut. The cutouts are preferably configured in such a way that they are arranged superposable in the connected state of the base body and of the reinforcement element.

According to a first embodiment of a spring strut top mounting of the present disclosure, the at least one separate reinforcement element is embodied as a piece of shaped sheet metal. It is particularly advantageous here if the reinforcement sheet metal is shaped in such a way that it is adapted to the shape of the base body at least in the vicinity of the stamped regions of the base body. This is because the base body and the reinforcement sheet metal can then be connected to one another in a particularly reliable fashion in terms of processing, and a local doubling of material over the entire region of the base area of the stamped regions can be ensured.

If the at least one base body and/or the at least one reinforcement element is embodied in a shell shape, it is particularly advantageous if the side regions of the connecting partners which are configured in a shell shape also lay one against the other. The region of the doubling of material can therefore be increased further and thus the rigidity of the assemblage can be improved further, in particular taking into account the installation space provided for the installation of a spring strut top mounting.

However, it is also conceivable for the reinforcement to be embodied as a planar plate which lays against the base body essentially in the vicinity of the stamped regions of the dome-shaped section. This embodiment also improves the rigidity of the spring strut and likewise has the specified advantages.

The base area of the stamped region or regions can be, for example, semi-circular-shaped or be in the shape of a rectangle or of a triangle. Any other shape is also suitable as long as a sufficiently large area is made available for the connection to the reinforcement element. The base area of the totality of the stamped regions in the base body make up at least 20%, preferably at least 40%, particularly preferably at least 60% of the area of the region connecting to the spring strut. As a result, a sufficiently large area can be made available for the connection to the reinforcement element.

The depth of the step-shaped stamped regions is to be set as a function of the materials used in a suitable way for the loading. If the base body has a plurality of stamped regions, it is also conceivable for the stamped regions to have different depths. In this way, the largest possible variation of the geometry of the base body, and therefore further improved rigidity of this component, can be made available. Of course, it is also advantageous if a plurality of stamped regions have the same depth. The reinforcement element can then be configured in a particularly simple way, since the connection in the region of the stamped regions does not require any complex geometry of the reinforcement element.

According to a further preferred embodiment, the at least one base body and the at least one reinforcement element are configured in such a way that, in the connected state, there is at least one cavity between the two components. The regions of the base body which are not used to connect to the reinforcement element are preferably arranged at a distance from the reinforcement element. By means of such an assemblage it is possible to make available a profile which, owing to the different geometries of the connecting partners, further improves the rigidity of this assembly without increasing the expenditure on material.

Furthermore, it is advantageous if the at least one reinforcement element has at least one stamped region, wherein the at least one stamped region is configured in such a way that, in the connected state, it lays superposable against the at least one stamped region of the base body. According to this embodiment of the spring strut top mounting, the reinforcement element also has increased rigidity as a result of the variation in the geometry, with the result that the rigidity of the spring strut top mounting can be improved further and the reduction in stress concentrations in this component can be increased further.

According to a further preferred configuration of the spring strut top mounting of the present disclosure, the at least one base body and the at least one reinforcement element form a closed profile. This can be achieved, for example, by virtue of the fact that both connecting elements are configured in a shell shape, wherein the shape of the reinforcement element is adapted to the shape of the base body in such a way that the reinforcement element lays against the base body both in the vicinity of the stamped regions of the base body and in the rest of the side region of the shell-shaped connecting partners. This configuration of the profile likewise improves the rigidity of this assemblage, since stresses in the material can be reduced in an optimal fashion, as a result of which the service life of the spring strut top mounting can be improved further.

The at least one reinforcement element preferably has greater strength than the at least one base body. For this purpose, the reinforcement element can be composed, for example, of a material which has greater strength than the material of the base body. This has the advantage that for the manufacture of the geometrically complex base body a material can be used which can be used as a result of a particularly good shaping behavior and therefore a comparatively low strength. If the reinforcement element is manufactured from a material which is particularly strong, sufficient strength of the assemblage can be ensured as a result.

In addition, the at least one reinforcement element can also have a greater material thickness than the at least one base body. The base body can have, for example, a thickness of 1.5 mm, while the reinforcement element has a thickness of 2 mm. Alternatively, the base body can have a thickness of 1.5 mm, while the thickness of the reinforcement element is 1.8 mm. Of course, it is also conceivable for both components to have the same thickness, in particular a thickness of 2 mm or a thickness of 1.5 mm.

However, the present invention is not restricted to components with a constant thickness. It is also conceivable for the base body and/or the reinforcement element to have a greater thickness, preferably in the region of high loading, particularly preferably in the region connecting to the spring strut, than, for example, in the regions which are subject to no loading or low loading. In this way, the configuration of the spring strut top mounting can be adapted further in a way which is suitable for the loading.

According to a further preferred configuration of the spring strut top mounting according to the invention, the at least one base body and/or the at least one reinforcement element are composed of steel, in particular of stainless steel or a deep drawing steel.

The at least one base body and/or the at least one reinforcement element preferably have drilled holes, in particular in the vicinity of the stamped regions, wherein the drilled holes are arranged in such a way that they are positioned one on top of the other superposable in the connected state of the two components. According to this configuration, the spring strut can be screwed particularly easily to the base body and at the same time to the reinforcement element.

The connection between the at least one base body and the at least one reinforcement element can be a materially joined or frictionally locking connection. It is conceivable that the connection partners are bonded, welded, soldered or screwed to one another.

The present disclosure is explained in further detail below with reference to the attached drawing figures.

FIG. 1 shows an exemplary embodiment of an inventive spring strut top mounting 2 composed of a shaping base body 4 with a dome-shaped section 6 and at least one separate, local reinforcement element 8 in an exploded illustration. In addition, the base body 4 has a region 3 connecting to the vehicle bodywork. Both the base body 4 and the local reinforcement element 8 each have a respective cutout 5, 7 for adjusting a spring strut, which strut is not shown in the drawing figures.

Figure 2:
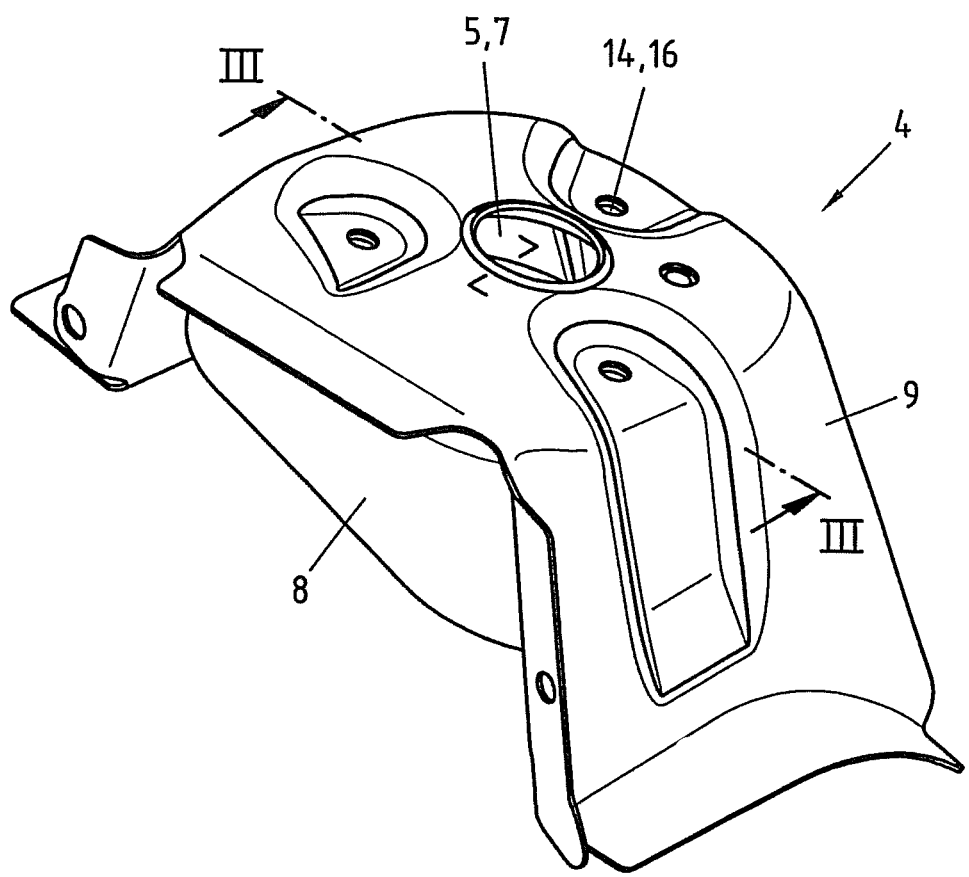
FIG. 2 is an isometric view of the assembled spring strut top mounting of FIG. 1.

The base body 4 also has one or more stamped regions 10, at which locations the reinforcement element 8 lays against the base body 4 when the components are assembled together, as shown in FIG. 2. In addition, the reinforcement element 8 also has one or more stamped regions 12 which are configured in such a way that, in the connected state, they lay superposable against the corresponding stamped regions 10 of the base body 4. The local rigidity of the spring strut top mounting can be considerably improved according to the invention both by means of the geometric configuration of the two components 4 and 8 and by means of the local doubling of material in the connected state of the components.

Both the base body 4 and the local reinforcement element 8 are shell shaped in the present exemplary embodiment. In such embodiment, the shape of the reinforcement element 8 is adapted to the shape of the base body 4 in such a way that, when they are coupled or connected together, the reinforcement element 8 lays, as illustrated in the embodiment shown in FIG. 2, against the base body 4 both in the vicinity of the stamped regions 10 of the base body, and in the remainder of the un-stamped side region 9 of the shell-shaped connection partners 4, 8.

According to the illustrated exemplary embodiment, the assembled base body 4 and the reinforcement element 8 together form a closed profile which also considerably improves the rigidity of the spring strut top mounting according to the invention. In the exemplary embodiment shown, the reinforcement element 8 is embodied as a piece of reinforcement sheet metal. The shape of the piece of reinforcement sheet metal 8 is adapted here, as already described, to the shape of the base body 4.

In the exemplary embodiment shown, the base body 4 has three stamped regions 10, wherein the base area of the totality of the stamped regions is approximately 50% of the base area of the dome-shaped section 6. The stamped regions 10 extend here both over the dome-shaped section 6 of the base body 4 and over the side region of the shell-shaped base body. As a result, it is possible to ensure that a sufficiently large area is available for the connection to the reinforcement element 8.

The piece of reinforcement sheet metal 8 here has greater strength and a greater material thickness than the base body. For example, the thickness of the reinforcement element is 2 mm, while the thickness of the base body is 1.5 mm. Alternatively, the thickness of the reinforcement element can also be 1.8 mm, and the thickness of the base body can be 1.5 mm.

In an advantageous manner, the base body 4 can then be manufactured from a material which makes available a particularly good shaping capability, with the result that the complex base body can be manufactured very easily. Nevertheless, owing to the high strength of the reinforcement element the assemblage composed of the base body 4 and reinforcement element 8 meets the requirements which are made of the spring strut top mounting in this respect. Furthermore, it is also conceivable for the base body and the reinforcement sheet metal to be of the same thickness.

Both the base body 4 and the reinforcement element 8 have drilled holes 14, 16, with the result that the spring strut can be screwed both to the base body 4 and to the reinforcement element 8.

The connection of the base body 4 to the reinforcement element 8 is preferably made available by means of a materially joined or frictionally locking connection. The base body 4 and the reinforcement element 8 can, for example, be bonded, welded, soldered or screwed to one another.

FIG. 2 shows the exemplary embodiment of a spring strut top mounting which is illustrated in FIG. 1, in the connected or assembled state. The reinforcement element lays here against the base body 4 in the interior of the base body 4 in the vicinity of the stamped regions 10 and in the vicinity of the sidewalls 9. The regions which are not provided for the connection to the reinforcement element are at a distance therefrom.

Consequently, at least one cavity is formed between the base body 4 and the reinforcement element 8. As a result of the coupling or connection of the base body 4 to the reinforcement element 8, it is possible to make available a profile which makes available increased rigidity, in particular increased local rigidity. Such increased rigidity results in, on the one hand, the increased reduction of stress in the spring strut top mounting and, on the other hand, the reduction of transmission of energy into the vehicle bodywork. The drilled holes 14, 16 and the cutouts 5, 7 defined in the respective base body 4 and the reinforcement element 8, which are provided to permit the spring strut to be mounted thereto, are preferably arranged superposable in the connected state of the two components. Consequently, a spring strut can be screwed to both the base body 4 and the reinforcement element 8 at the same time.

Figure 3:
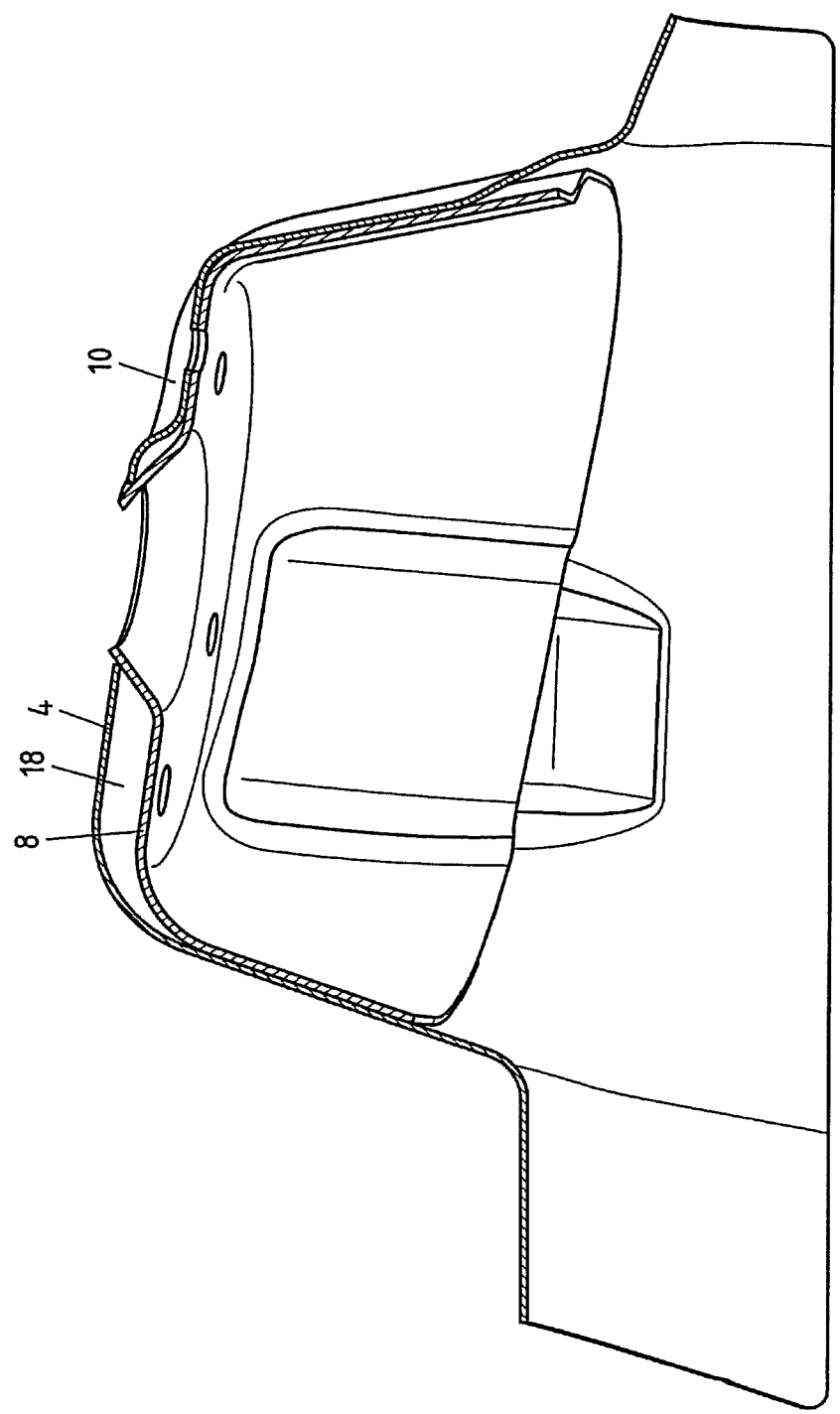
FIG. 3 is a side cross-section view, taken about section line of the assembled spring strut top mounting of FIG. 2.

FIG. 3 shows a sectional illustration through the sectional line of the exemplary embodiment of an inventive spring strut top mounting which is illustrated in FIG. 2. The sectional view shows the assembly comprising the base body 4 and the reinforcement element 8. The base body 4 has a stamped region 10 which extends over the dome-shaped section 6 and over the side region of the base body 4. The reinforcement element 8 is connected to the base body 4 in the vicinity of the stamped region 10. In addition, the spring strut top mounting has a cavity 18 in the vicinity of the base body 4 which is not used for the connection to the reinforcement element 8. As a result of the connection of the base body and of the reinforcement element 8, it is possible to make available a profile, in particular a closed profile, by means of which the rigidity of the spring strut dome is increased and in this respect the reduction of stresses in the material is improved.

What is claimed is:

1. A spring strut top mounting for mounting to a spring strut of a vehicle, comprising:
    at least one base body having,
        a dome-shaped section defined in a region that is configured to be coupled to the spring strut, and
        stamped regions formed in the region configured to be coupled to the spring strut; and
    at least one separate local reinforcement element coupled to said at least one base body and laying against said at least one base body at least in a vicinity of the stamped regions.

2. The spring strut top mounting of claim 1, wherein said at least one reinforcement element is shaped sheet metal.

3. The spring strut top mounting of claim 1, wherein at least one of said at least one base body and at least one reinforcement element are shell shaped.

4. The spring strut top mounting of claim 1, wherein a base area of all of the stamped regions in the at least one base body occupies at least 20% of the total area in the region configured to be coupled to the spring strut.

5. The spring strut top mounting of claim 1, wherein said at least one base body coupled to said at least one reinforcement element defines a cavity there between.

6. The spring strut top mounting of claim 1, wherein said at least one reinforcement element has at least one stamped region configured to lay superposable against at least one of the stamped regions of said base body.

7. The spring strut top mounting of claim 1, wherein said at least one base body and said at least one reinforcement element form a closed profile.

8. The spring strut top mounting of claim 1, wherein said at least one reinforcement element has a greater strength than said at least one base body.

9. The spring strut top mounting of claim 1, wherein said at least one reinforcement element has a greater material thickness than the at least one base body.

10. The spring strut top mounting of claim 1, wherein one or more of said at least one base body and said at least one reinforcement element are made of steel.

11. The spring strut top mounting of claim 1, wherein said at least one base body and said at least one reinforcement element each have one or more holes defined therein, and wherein said holes are configured such that, when said base body and reinforcement element are coupled together, at least one hole in said base body is positioned superposable on top of at least one hole in said reinforcement element.

12. The spring strut top mounting of claim 1, wherein said at least one base body and said at least one reinforcement element are coupled together by one of a materially joined or frictionally locking connection.

13. A spring strut top mounting for mounting to a spring strut of a vehicle, comprising:
    at least one base body having,
        a dome-shaped section defined in a region that is configured to be coupled to the spring strut, and
        a plurality of step-shaped stamped regions formed in the region configured to be coupled to the spring strut; and
    at least one separate local reinforcement element coupled to said at least one base body and laying against said at least one base body at least in a vicinity of at least one of said plurality of stamped regions.

14. The spring strut top mounting of claim 13 wherein at least two of the stamped regions have different depths as measured from a surface of the at least one base body.

15. The spring strut top mounting of claim 13, wherein a base area of the sum of the plurality of stamped regions in the at least one base body occupies at least 20% of the total area in the region configured to be coupled to the spring strut.

16. The spring strut top mounting of claim 13 wherein each of the plurality of stamped regions is configured as a basin that sits below a surface of the at least one base body.

17. The spring strut top mounting of claim 13, wherein said at least one separate local reinforcement element has at least one stamped region configured to lay superposable against said at least one of said plurality of stamped regions of said base body.

18. The spring strut top mounting of claim 13, wherein said at least one base body and said at least one reinforcement element form a closed profile.

19. The spring strut top mounting of claim 13, wherein said at least one reinforcement element has a greater strength than said at least one base body.

* * * * *